United States Patent [19]

Di Bella

[11] 4,031,146

[45] June 21, 1977

[54] PROCESS FOR THE PRODUCTION OF 2,5-DICHLOROTOLUENE

[75] Inventor: Eugene P. Di Bella, Piscataway, N.J.

[73] Assignee: Tenneco Chemicals, Inc., Saddle Brook, N.J.

[22] Filed: Mar. 22, 1976

[21] Appl. No.: 669,439

[52] U.S. Cl. .......................................... 260/650 R
[51] Int. Cl.² ........................................ C07C 25/04
[58] Field of Search ............................... 260/650 R

[56] References Cited

UNITED STATES PATENTS

| | | | |
|---|---|---|---|
| 1,946,040 | 2/1934 | Stoesser et al. | 260/650 R |
| 3,000,975 | 9/1961 | Di Bella | 260/650 R |
| 3,226,447 | 12/1965 | Bing et al. | 260/650 R |

*Primary Examiner*—D. Horwitz
*Attorney, Agent, or Firm*—Evelyn Berlow

[57] ABSTRACT

Dichlorotoluene that contains at least 55 percent of 2,5-dichlorotoluene is prepared by contacting ortho-chlorotoluene with chlorine in the presence of a chlorination catalyst that is either a metal sulfide or a mixture of a ring-chlorination catalyst and a co-catalyst that is a sulfur compound to form a reaction mixture containing ortho-chlorotoluene, dichlorotoluene, and trichlorotoluene and separating dichlorotoluene from the reaction mixture.

14 Claims, No Drawings

PROCESS FOR THE PRODUCTION OF 2,5-DICHLOROTOLUENE

This invention relates to a process for the production of dichlorotoluenes. More particularly, it relates to a process for the chlorination of ortho-chlorotoluene whereby there is formed a mixture of dichlorotoluene isomers of unusually high 2,5-dichlorotoluene content.

2,5-Dichlorotoluene is used commercially as an intermediate in the production of compounds that are useful as pesticides, lubricants, and dyestuffs. For example, it is used in the production of 2,5-dichlorobenzoic acid, which is then converted to 2,5-dichloro-3-aminobenzoic acid, which is a widely-used herbicide.

In the past, 2,5-dichlorotoluene has been produced by the diazotization of 5-chloro-2-aminotoluene and the treatment of the resulting intermediate compound with cuprous chloride. It has also been produced by the direct chlorination of toluene or orthochlorotoluene in the presence of iron or another known ring-chlorination catalyst. This process, which is described in my U.S. Pat. No. 3,000,975, yields a mixture of dichlorotoluenes that contains about 30 percent to 50 percent of 2,5-dichlorotoluene. In view of the increasing demand for 2,5-dichlorotoluene, it has become necessary to provide a more efficient process for the production of a dichlorotoluene product that contains a substantially larger amount of 2,5-dichlorotoluene than is obtained when ortho-chlorotoluene is chlorinated in the presence of the previously-known ring-chlorination catalysts.

In accordance with this invention, it has been found that when ortho-chlorotoluene is chlorinated in the presence of any of the previously-known ring-chlorination catalysts and a co-catalyst that is sulfur or a compound containing divalent sulfur the dichlorotoluene mixture formed has a 2,5-dichlorotoluene content that is substantially higher than that obtained when the chlorination is carried out in the absence of the co-catalyst.

The process of this invention is carried out by contacting ortho-chlorotoluene with chlorine in the presence of a ring-chlorination catalyst and a co-catalyst as hereinafter defined until the reaction product is a mixture of chlorotoluenes that contains at least 50 percent of dichlorotoluenes. This mixture is then fractionally distilled to separate the dichlorotoluenes from the monochlorotoluene and trichlorotoluenes that are present. The dichlorotoluene fraction, which contains at least 55 percent of 2,5-dichlorotoluene, may be subjected to fractional distillation or crystallization to obtain substantially pure 2,5-dichlorotoluene.

The chlorination of ortho-chlorotoluene is carried out in the presence of a ring-chlorination catalyst and a co-catalyst that is sulfur or a compound containing divalent sulfur. Any of the well-known ring-chlorination catalysts that are used in the production of chlorobenzenes and chlorotoluenes may be used. These include, for example, iron, iron chlorides, ferrocene, aluminum chloride, zirconium tetrachloride, thallium chloride, stannic chloride, gallium chloride, indium chloride, tungsten chloride, molybdenum chloride, iodine, and boron trifluoride and mixtures thereof. The preferred ring-chlorinated catalysts and the ones ordinarily used in the process of this invention are iron, ferrocene, zirconium tetrachloride, and aluminum chloride.

The sulfur compounds that can be used as co-catalysts in the process of this invention include sulfur and a wide variety of organic and inorganic compounds that contain one or more divalent sulfur atoms and that are soluble to at least a limited extent in the reaction mixture. These include sulfur, sulfur monochloride, sulfur dichloride, carbon disulfide, thiophenes, thiophanes, alkyl-, cycloalkyl-, aryl-, and aralkyl mercaptans and dimercaptans, thioethers, and the like. The preferred co-catalysts are sulfur monochloride, sulfur, and the sulfur-containing compounds that are converted to sulfur monochloride under the conditions of ring-chlorination, for example, sulfur dichloride and carbon disulfide.

When ring-chlorination catalysts that possess only moderate activity, such as stannic chloride, thallium chloride, and indium trichloride, are used, the co-catalyst appears to improve the utilization of chlorine during the chlorination reaction as well as to shift the isomer ratio distribution of the dichlorotoluene fraction to favor 2,5-dichlorotoluene formation.

In a preferred embodiment of this invention, the combination of ring-chlorination catalyst and co-catalyst is replaced by a metallic sulfide. The useful metal sulfides, which contain at least one divalent sulfur atom, are sulfides of the aforementioned metals whose chlorides are ring-chlorination catalysts. Particularly advantageous results have been obtained using ferrous sulfide, ferric sulfide, stannic sulfide, and indium sesquisulfide. The metal sulfides may be added to the reaction mixture as such, or they may be formed in situ by the reaction of the metal chloride that is being used as the ring-chlorination catalyst with the sulfur compound that is the co-catalyst.

The catalyst system must contain at least 0.1 part by weight of the co-catalyst per part by weight of the ring-chlorination catalyst if the desired high proportion of 2,5-dichlorotoluene is to be obtained. In most cases, 0.5 part to 1.0 part by weight of the co-catalyst is used per part by weight of the ring-chlorination catalyst. The use of a larger amount of the co-catalyst does not result in a further increase in the yield of the dichlorotoluene fraction or its 2,5-isomer content.

The amount of the catalyst system that is used in the process of this invention is not critical. It is that which will produce in good yield a dichlorotoluene fraction that contains at least 55 percent of the 2,5-isomer. At least 0.1 gram of the ring-chlorination catalyst or metal sulfide is usually used per mole of ortho-chlorotoluene. An amount of the catalyst system that will provide from 0.5 gram to 1.0 gram of the ring-chlorination catalyst or metal sulfide per mole of ortho-chlorotoluene is generally preferred because it makes possible a reaction rate that is fast enough for commercial operation of the process while inhibiting side-chain chlorination and ring-addition reactions The chlorination of ortho-chlorotoluene is carried out by procedures that are well known in the art. For example, chlorine may be added to a reaction mixture containing ortho-chlorotoluene and the catalyst system until the increase in the weight of the reaction mixture or in its specific gravity indicates that the desired amount of chlorine has reacted with the ortho-chlorotoluene. When the chlorination is continued until from about 0.5 gram atom to 0.9 gram atom of chlorine has reacted per mole of ortho-chlorotoluene, the reaction product generally contains from 50 to 75 percent by weight of dichlorotoluene, 20 to 45 percent by weight of monochlorotoluene, and 2 to 10 percent by weight of trichlorotoluene. It preferably contains at least 65 percent by weight of dichlorotoluene and not more than 6 percent by weight of trichlorotoluenes. The dichlorotoluene, which may be separated from the monochlorotoluene and trichlorotoluene by fractional distillation or other known technique, contains at least 55 percent and preferably 60 percent or more 2,5-dichlorotoluene, the remainder being 2,3-, 2,4-, and 2,6-dichlorotoluenes. 2,5-Dichlorotoluene may be separated from its isomers, for example, by fractional distillation or fractional crystallization.

The chlorination is carried out at temperatures in the range of −20° C. to 70° C., with 20° C. to 50° C. the preferred range. At temperatures below −20° C., the reaction takes place too slowly to be of commercial interest. At temperatures above 70° C., there is a tendency for side-chain chlorinated reaction by-products to form. Since chlorination is an exothermic reaction, external cooling may be required to maintain the reaction temperature in the desired range.

The rate at which chlorine is added to the reaction mixture does not have an appreciable effect on the yield of dichlorotoluene or on the isomer distribution of the product.

The invention is further illustrated by the following examples.

EXAMPLES 1-8

A series of ring chlorinations of ortho-chlorotoluene was carried out in the presence of various catalysts according to the following general procedure:

A mixture of 253 grams (2.0 moles) of ortho-chlorotoluene and a catalyst in a glass chlorination vessel was chlorinated by passing a stream of chlorine over its surface at the rate of about 60 grams per hour until from 100 to 116 grams of chlorine (0.70–0.82 mole $Cl_2$ per mole of o-chlorotoluene) had been added. During the chlorination, the reaction mixture was stirred, and its temperature was maintained at 34°–36° C. by means of external cooling. Samples of the chlorination mixture were analyzed by gas-liquid chromatography. The catalysts used and the results obtained are summarized in Table I.

COMPARATIVE EXAMPLES A-H

For comparative purposes, a number of known ring-chlorination catalysts were used in the chlorination of ortho-chlorotoluene by the procedure described above. The catalysts used and the results obtained are summarized in Table II.

From the data in Tables I and II, it will be seen that when a catalyst system that comprises either a ring-chlorination catalyst and a sulfur co-catalyst or a metal sulfide is used in place of the previously-known ring-chlorination catalysts in the chlorination of ortho-chlorotoluene, there is an increase in the yield of dichlorotoluene as well as an increase in the 2,5-dichlorotoluene content of the dichlorotoluene fraction.

Table I

| Ex. No. | Catalyst Composition | Amount of Catalyst (g. per mole of o-Cl toluene) | Chlorine Charged (moles $Cl_2$ per mole of o-Cl toluene) | Chlorination Level (gram atoms of Cl substd. per mole of o-Cl toluene) | Product Composition (% by wt.)* | | | Isomer Distribution in Dichlorotoluene (%) | | | |
|---|---|---|---|---|---|---|---|---|---|---|---|
| | | | | | Mono-chloro-toluene | Di-chloro-toluene | Tri-chloro-toluene | 2,3- | 2,4- | 2,5- | 2,6- |
| 1 | Fe | 0.5 | 0.72 | 0.68 | 29.6 | 66.2 | 4.2 | 13.6 | 16.6 | 58.5 | 11.3 |
| 2 | $S_2Cl_2$ Ferrocene | 0.5 1.0 | 0.71 | 0.66 | 30.9 | 65.4 | 3.7 | 12.3 | 16.0 | 61.6 | 10.1 |
| 3 | $S_2Cl_2$ $AlCl_3$ | 0.5 1.0 | 0.73 | 0.70 | 28.2 | 69.8 | 4.0 | 13.3 | 15.8 | 60.0 | 10.6 |
| 4 | $S_2Cl_2$ $ZrCl_4$ | 1.0 0.5 | 0.70 | 0.70 | 27.2 | 69.3 | 3.5 | 12.6 | 15.8 | 61.8 | 9.8 |
| 5 | $S_2Cl_2$ TlCl | 0.5 0.5 | 0.82 | 0.76 | 23.2 | 71.3 | 5.5 | 10.8 | 17.3 | 56.5 | 15.8 |
| 6 | $S_2Cl_2$ FeS | 0.5 1.0 | 0.81 | 0.81 | 19.7 | 74.3 | 6.0 | 12.0 | 16.4 | 60.8 | 10.8 |
| 7 | $Fe_2S_3$ | 0.75 | 0.74 | 0.54 | 41.8 | 56.1 | 2.1 | 12.0 | 16.7 | 57.4 | 13.9 |
| 8 | $In_2S_3$ | 1.0 | 0.82 | 0.75 | 24.1 | 71.1 | 4.8 | 10.9 | 17.0 | 60.0 | 12.1 |

*The gas-liquid chromatography data have been normalized to exclude the <0.5% of volatile materials added with the catalyst components.

Table II

Comparative Examples

| Ex. No. | Catalyst Composition | Amount of Catalyst (g. per mole of o-Cl toluene) | Chlorine Charged (moles $Cl_2$ per mole of o-Cl toluene) | Chlorination Level (gram atoms of Cl substd. per mole of o-Cl toluene) | Product Composition (%)* | | | | Isomer Distribution in Dichlorotoluene (%) | | | |
|---|---|---|---|---|---|---|---|---|---|---|---|---|
| | | | | | Mono-chloro-toluene | Di-chloro-toluene | Tri-chloro-toluene | Other ** | 2,3- | 2,4- | 2,5- | 2,6- |
| A | Fe | 0.5 | 0.74 | 0.73 | 27.4 | 65.7 | 6.9 | 0 | 14.9 | 19.4 | 35.8 | 29.9 |
| B | Ferrocene | 1.0 | 0.72 | 0.54 | 42.5 | 53.6 | 3.9 | 0 | 14.4 | 24.9 | 31.8 | 28.9 |
| C | Ferrocene Ethylene-diamine | 1.86 1.2 | 0.70 | 0.32 | 63.7 | 34.4 | 1.9 | 0 | 10.6 | 20.1 | 54.4 | 14.8 |
| D | $AlCl_3$ | 1.0 | 0.71 | 0.71 | 30.3 | 60.1 | 9.2 | 0.4 | 15.3 | 17.9 | 31.4 | 35.4 |
| E | $AlCl_3$ Ethylene-diamine | 1.0 | 0.73 | 0.31 | 65.4 | 32.1 | 2.5 | 0 | 13.6 | 19.0 | 39.5 | 28.1 |
| F | $ZrCl_4$ | 1.0 | 0.72 | 0.72 | 27.6 | 66.5 | 5.9 | 0 | 13.6 | 18.3 | 37.6 | 30.5 |
| G | TlCl | 1.0 | 0.81 | 0.58 | 38.1 | 59.3 | 2.6 | 0 | 13.2 | 18.7 | 46.7 | 21.4 |
| H | $InCl_3$ | 1.0 | 0.75 | 0.13 | 83.8 | 15.9 | 0.3 | 0 | 16.4 | 19.2 | 44.0 | 20.4 |

*The gas-liquid chromatography data have been normalized to exclude the <0.5% of volatile materials present in some catalyst components.
**Principally tetrachlorotoluene and o-chlorobenzyl chloride.

What is claimed is:

1. The process for the production of dichlorotoluene containing at least 55 percent of 2,5-dichlorotoluene which comprises contacting ortho-chlorotoluene with chlorine until from about 0.5 gram atom to 0.9 gram atom of chlorine has reacted per mole of ortho-chlorotoluene in the presence of a catalyst selected from the group consisting of
   a. a ring-chlorination catalyst selected from the group consisting of iron, ferrocene, chlorides of iron, aluminum, zirconium, thallium, tin, indium, molybdenum, gallium, and tungsten and mixtures thereof and a co-catalyst selected from the group consisting of sulfur, sulfur monochloride, sulfur dichloride, and carbon disulfide in the amount of at least 0.1 part by weight of the ring-chlorination catalyst;
   b. a sulfide of a metal selected from the group consisting of iron, aluminum, zirconium, thallium, tin, indium, molybdenum, gallium, and tungsten and mixtures thereof; and
   c. mixtures thereof, in the amount of at least 0.1 gram of the ring-chlorination catalyst or metal sulfide per mole of ortho-chlorotoluene and at a temperature in the range of −20° C. to 70° C. to form a reaction mixture that contains from 50 percent to 75 percent by weight of dichlorotoluenes and separating from said reaction mixture a dichlorotoluene fraction containing at least 55 percent of 2,5-dichlorotoluene.

2. The process of claim 1 wherein the catalyst comprises a ring-chlorination catalyst selected from the group consisting of iron, ferrocene, chlorides of iron, aluminum, zirconium, thallium, tin, indium, and molybdenum, gallium, tungsten, and mixtures thereof and a co-catalyst selected from the group consisting of sulfur, sulfur monochloride, sulfur dichloride, and carbon disulfide in the amount of 0.5 part to 1.0 part by weight of the co-catalyst per part by weight of the ring-chlorination catalyst.

3. The process of claim 2 wherein the ring-chlorination catalyst is iron.

4. The process of claim 2 wherein the ring-chlorination catalyst is ferrocene.

5. The process of claim 2 wherein the ring-chlorination catalyst is zirconium tetrachloride.

6. The process of claim 2 wherein the ring-chlorination catalyst is aluminum chloride.

7. The process of claim 2 wherein the co-catalyst is sulfur monochloride.

8. The process of claim 1 wherein the catayst comprises a sulfide of a metal selected from the group consisting of iron, aluminum, zirconium, thallium, tin, indium, molybdenum, gallium, tungsten, and mixtures thereof.

9. The process of claim 8 wherein the catalyst is an iron sulfide.

10. The process of claim 8 wherein the catalyst is indium sesquisulfide.

11. The process of claim 1 wherein the amount of catalyst used is that which will provide from 0.5 gram to 1.0 gram of the ring-chlorination catalyst or metal sulfide per mole of ortho-chlorotoluene.

12. The process of claim 1 wherein the chlorination is carried out at a temperature in the range of 20° C. to 50° C.

13. The process of claim 1 wherein the chlorination is continued until the reaction mixture contains at least 65 percent of dichlorotoluenes.

14. The process of claim 1 wherein the dichlorotoluene fraction is fractionally distilled to obtain substantially pure 2,5-dichlorotoluene.

* * * * *

UNITED STATES PATENT AND TRADEMARK OFFICE
CERTIFICATE OF CORRECTION

PATENT NO. : 4,031,146
DATED : June 21, 1977
INVENTOR(S) : Eugene P. DiBella

It is certified that error appears in the above-identified patent and that said Letters Patent are hereby corrected as shown below:

Column 5, line 16, after "by weight of" insert

-- the co-catalyst per part by weight of --.

Signed and Sealed this

Eighteenth Day of October 1977

[SEAL]

Attest:

RUTH C. MASON
Attesting Officer

LUTRELLE F. PARKER
Acting Commissioner of Patents and Trademarks